United States Patent [19]
Rey et al.

[11] 4,056,095
[45] Nov. 1, 1977

[54] CONTROL DEVICE FOR MEDICAL AND SURGICAL USES

[75] Inventors: Pierre Théodore Joseph Rey, Thorigny; Jacqueline Agathe Marie Leandri, Paris; Clément Claude Abbou, Fontenay S/Bois, all of France

[73] Assignee: Agence Nationale de Valorisation de la Recherche (ANVAR), France

[21] Appl. No.: 672,680

[22] Filed: Apr. 1, 1976

[30] Foreign Application Priority Data

Apr. 4, 1975 France .................. 75.10534

[51] Int. Cl.² .................. A61F 1/00; A61B 17/00
[52] U.S. Cl. .................. 128/1 R; 128/DIG. 25; 128/260; 417/389; 417/472; 3/1
[58] Field of Search ....... 128/214 R, 214 F, DIG. 25, 128/214.2, 1 R, 260, 2 F, 350 R; 417/380, 389, 472, 473, 207; 3/1; 222/386.5

[56] References Cited

U.S. PATENT DOCUMENTS

| | | | |
|---|---|---|---|
| 2,464,095 | 3/1949 | Nies | 417/389 X |
| 2,494,393 | 1/1950 | Lamson | 128/DIG. 25 |
| 2,663,363 | 12/1953 | Krautter | 417/472 X |
| 3,731,681 | 5/1973 | Blackshear et al. | 128/214 F |
| 3,750,194 | 8/1973 | Summers | 128/1 R X |
| 3,815,576 | 6/1974 | Balaban | 128/DIG. 25 |
| 3,841,304 | 10/1974 | Jones | 128/1 R |
| 3,863,622 | 2/1975 | Buuck | 128/1 R |
| 3,951,147 | 4/1976 | Tucker et al. | 128/260 |

OTHER PUBLICATIONS

IEEE Transactions On Bio-Medical Engr. Oct. 1970, Intermittant Occlusion System, Timm et al., p. 352.
Trans. Amer. Soc. Artif. Organs, 1971, pp. 132, 133 & 141, Artificial Urethral Sphincter, Hargest et al.

*Primary Examiner*—Aldrich F. Medbery
*Attorney, Agent, or Firm*—Craig & Antonelli

[57] ABSTRACT

A control device in implantable sub-cutaneously for use in medicine and surgery. It is actuable by pressing on a sub-cutaneous membrane. It comprises a first chamber closed by the membrane which is placed on one surface of its casing and contains an incompressible fluid, and a second chamber, containing a gas and housing two coaxial bellows connected at their free ends. One of the bellows communicates with the first chamber and the second bellows communicates with a flexible duct going to the duct or cavity to be controlled.

22 Claims, 3 Drawing Figures

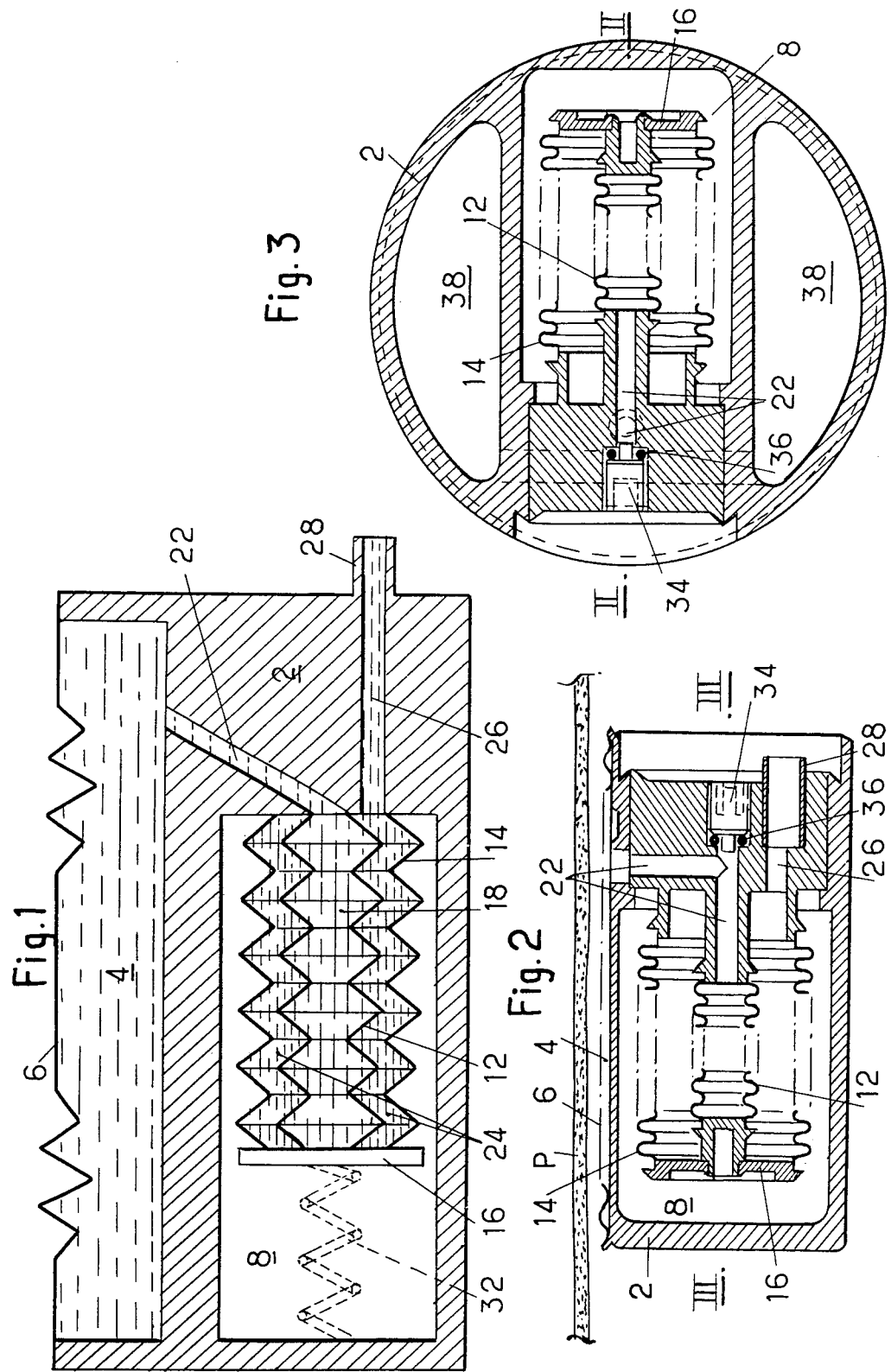

CONTROL DEVICE FOR MEDICAL AND SURGICAL USES

BACKGROUND OF THE INVENTION

There exist in medicine, surgery and biology, artificial sphincters designed to replace natural sphincters such as those of the bladder or of the anus or to be placed in the natural or artificial ducts of living organisms. Such an artificial sphincter is, for example, described in French Patent Application No. 73, 40939 of Nov. 16, 1973, filed in the name of AGENCE NATIONALE DE VALORISATION DE LA RECHERCHE - ANVAR -; this artificial sphincter is actuated by the displacement of a small volume of fluid, preferably a liquid.

The present invention relates to a control for such an artificial sphincter or the like, which control is implantable in a sub-cutaneous position and can be actuated by pressure, for example, manual or digital, on the skin. More generally, such a control is adapted to control the closing and opening of intra-corporal orifices usually including a sphincter, and to control generally the elimination or the flow of liquid or semi-liquid substances contained in the natural or artificial intra-corporal ducts or cavities.

GENERAL DESCRIPTION OF THE INVENTION

According to the invention there is provided an externally actuated control device for medical and surgical uses, comprising within a casing, a first chamber, closed by a membrane positioned on one face of the casing and containing an incompressible fluid, and a second chamber, containing a gas and housing two coaxial bellows joined together at their free ends, one of the two bellows communicating with said first chamber and the second bellows communicating with a flexible duct going to the duct or the cavity to be controlled, possibly through an artificial sphincter or the like.

A pressure, for example manual or digital, on the skin is transmitted to said membrane, which bends thereby decreasing the volume of the first chamber: incompressible fluid passes into the first bellows, which is stretched, and stretches the second bellows, which sucks through the inlet-outlet and the flexible duct, fluid for actuating the sphincter or for controlling an intra-corporal duct or cavity, and this by slightly compressing the gas of the second chamber.

Besides the foregoing features, the invention comprises also other features which will become apparent from the following description.

According to other aspects of the invention, there are provided not only novel implantable control means, for medical or surgical uses, but also the means adapted for their production and assemblies comprising said control means.

BRIEF DESCRIPTION OF THE DRAWINGS

The invention will be better understood from the further description which follows, referring to the accompanying drawing in which:

FIG. 1 is a diagrammatic section of one embodiment of a control device according to the present invention, applied to an artificial sphincter; and FIGS. 2 and 3 are two perpendicular cross-sections, FIG. 2 being along the line II—II of FIG. 3 and FIG. 3 being along the line III—III of FIG. 2, of a preferred embodiment of a control device according to the invention.

It must be understood, however, that this drawing and the corresponding description are given purely by way of illustration of the invention and do not constitute in any way a limitation thereof.

DESCRIPTION OF PREFERRED EMBODIMENTS

The embodiment of the control device shown in diagrammatic cross-section in FIG. 1 comprises, in a casing 2, a first chamber 4, closed by a membrane 6 positioned on one face of the casing 2. This membrane 6 may be constituted by a thin elastic sheet, possibly including undulations, as shown. The first chamber 4 is filled with an incompressible fluid. In the casing 2, a second chamber 8, containing a gas, houses two coaxial bellows 12 and 14, fixed by one end to a wall of the second chamber 8, and joined together at their free ends by a free plate 16. The first bellows is here the inner bellows 12, whose inner space 18 communicates with the first chamber 4 through a passage 22. The second bellows is the outer bellows 14, whose annular space 24 communicates through a passage 26 with a lateral inlet-outlet 28 serving as a nozzle for a flexible duct (not shown).

The elasticity of the compressed gas in the second chamber 8 ensures the return of the members to their initial positions and outward flow through inlet-outlet when the pressure on the membrane 6 is released, and hence the reclosing of the sphincter. If desired, it is possible, for this return, to fit the plate 16 with a return spring 32, housed in the second chamber 8 (and shown in discontinuous lines in FIG. 1).

The present invention provides for a choice of the ratio of the diameters of the two bellows 12 and 14, in order to effect according to considerations of practice or convenience, a selected hydraulic transmission ratio. Purely by way of indication, a variation in volume of about 0.5 cm$^3$ of the bellows 12 can thus control a variation in volume of about 1.5 cm$^3$ at the inlet-outlet 28 ( and at the ballonet of said sphincter not illustrated in the drawings but similar to the one shown in FIG. 1 of the U.S. Pat. to Lamson No. 2,494,393 of Jan. 10, 1959 as an inflatable balloon 13 as described in lines 37 and 38 of column 2 or another amplification of the volume displaced.

In the preferred embodiment of the invention shown in FIGS. 2 and 3, the casing 2 is generally disc-shaped, lodged beneath the skin P of the patient with the membrane 6 immediately next to the latter (FIG. 2); this flat disc shape may be replaced by the shape of a cylinder, of a lens or of an ovoid. The two bellows 12 and 14 are produced, in known manner, by electrodeposition of a metal on a mandrel which is then removed. The plate 16 is in two pieces, on which the two bellows are welded and which are then welded together. The passage 22 is formed by two perpendicular holes and after the initial filling of the first chamber 4, their outlet is closed by a welded or screwed plug 34 with fluid-tightness by a toric seal 36. Recesses 38 (FIG. 3) lighten the assembly. The parts are made of stainless steel and are assembled by welding, for example, electric welding under argon. Purely by way of indication, the embodiment shown has a diameter of about 50 mm and a thickness of about 23 mm.

It will be apparent from the foregoing description that whatever the embodiments and applications adopted, the invention provides an implantable control device, for medical and surgical uses, which has with respect to previously known control devices for the same purposes, considerable advantages, and notably that of being applicable, besides the application described in the foregoing, to the control of the elimination or of the flow of liquid or semi-liquid substances contained in intracorporal cavities or passages. The invention is particularly useful for controlling the elimination of the cephalo-rachidial liquid in the treatment of hydrocephalus, of bile in the choledochal canal, or for controlling the flow of body fluids in the body cavities or passages in pharmacodynamics or in experimental surgery carried out on animals.

Thus, as emerges from the foregoing, the invention is in no way limited to those of its embodiments or types of application which have just been explicitly described; it encompasses, on the contrary, any modifications which may occur to the technician skilled in the art, without departing from the framework or scope of the invention. For example, the two bellows may be placed in extension of one another, the second bellows being filled with compressible fluid, and the second chamber communicating with the inlet-outlet 28.

WE CLAIM:

1. An externally actuated control device for operating a means for controlling a body duct or cavity in medical and surgical uses, implantable in sub-cutaneous position and actuatable by pressing on a sub-cutaneous membrane, said device comprising, in a casing, a first chamber, closed by said membrane which is positioned on one face of the casing and containing an incompressible fluid, and a second chamber, containing a gas and housing two coaxial bellows joined together at their free ends, one of the two bellows being an actuating bellows and communicating with said first chamber containing said incompressable fluid, and the second bellows with a flexible control duct going to said body duct or cavity to be controlled.

2. Control device according to claim 1, wherein the two bellows are fixed by one end to a wall of the second chamber and are joined together at their free ends by a free plate, the first bellows being the inner bellows and the second bellows being the outer bellows.

3. An externally actuated control device for medical and surgical uses, implantable in sub-cutaneous position and actuatable by pressing on a sub-cutaneous membrane, said device comprising, in a casing, a first chamber, closed by said membrane which is positioned on one face of the casing and containing an incompressible fluid, and a second chamber, containing a gas and housing two coaxial bellows joined together at their free ends, one of the two bellows being an actuating bellows and communicating with said first chamber containing said incompressable fluid, and the second bellows being an actuated bellows having a second fluid in communication with a flexible control duct going to said duct or cavity to be controlled,
    wherein the two bellows are fixed by one end to a wall of the second chamber and are joined together at their free ends by a free plate, the first bellows being the inner bellows and the second bellows being the outer bellows, and
    wherein the second chamber houses a return spring bearing against said free plate.

4. Control device according to claim 2, wherein the ratio of the diameters of the two bellows is selected to produce a predetermined hydraulic transmission ratio.

5. Control device according to claim 1, wherein said casing is housed under the skin of the patient, with said membrane immediately close to the latter.

6. Control device according to claim 1, in combination with artificial sphincter means.

7. Control device according to claim 6, wherein said sphincter comprises an inflatable ballonet mounted laterally in a portion of tube lodged in the natural body duct concerned, and a fluid-tight casing which is replaced by the control device, which actuates said inflatable ballonet through said flexible duct.

8. A control device for controlling implanted medical and surgical apparatus, said control device comprising
    a housing defining first and second chambers, said first chamber containing an incompressible fluid, and said second chamber containing a gas,
    first and second coaxial bellows arranged within said second chamber containing said incompressable fluid, said first and second bellows being operatively connected to axially move together,
    passage means in said housing for communicating said first chamber with the interior of said first bellows,
    actuating means for reversibly flowing said incompressible fluid between said first chamber and the interior of said first bellows through said passage means, and
    means communicating the interior of said second bellows with the medical and surgical apparatus to be controlled,
    wherein said control device is implanted in a subcutaneous position, and wherein said control device is actuated by manually pressing on the sub-cutaneously disposed actuating means.

9. A control device according to claim 8, wherein said actuating means includes an elastic membrane arranged at a surface of said housing to close said first chamber, and wherein said first chamber is filled with said incompressible liquid.

10. A control device according to claim 8, wherein each of said first and second bellows has a first end fixed to said housing at a wall portion which forms a part of said second chamber, and each of said first and second bellows has a second end fixed to a member being movable within said chamber.

11. A control device according to claim 10, wherein said passage means communicates with said interior of said first bellows through said wall portion of said housing, and said communicating means for second bellows extends through said wall portion.

12. A control device according to claim 11, wherein said passage means comprises two perpendicular ducts in said housing wall portion, one of said ducts extending to a filler aperture being sealable by a sealing means.

13. A control device according to claim 12, wherein said communicating means includes a further duct extending through said housing wall portion, an outlet nozzle at the exterior of said housing, and a flexible conduit extending from said nozzle to said medical and surgical apparatus to be controlled.

14. A control device according to claim 12, wherein said housing has a flat-cylindrical, disc-like construction with said first chamber being disposed at a major disc surface.

15. A control device according to claim 14, wherein said actuating means includes an elastic membrane arranged at said major disc surface of said housing to close said first chamber, and wherein said first chamber is filled with said incompressible fluid.

16. A control device according to claim 15, wherein said elastic membrane is disposed immediately under the skin such as to be moved by pressing the skin.

17. A control device according to claim 8, wherein said passage means comprises two perpendicular ducts in said housing, one of said ducts extending to a filler aperture being sealable by a sealing means.

18. A control device according to claim 8, wherein said communicating means includes a further duct extending through said housing, an outlet nozzle at the exterior of said housing, and a flexible conduit extending from said nozzle to said nozzle to said medical and surgical apparatus to be controlled.

19. A control device according to claim 8, wherein said housing has a flat-cylindrical, disc-like construction with said first chamber being disposed at a major disc surface.

20. A control device according to claim 8, wherein said communicating means reversibly communicates a fluid between said second bellows and said medical and surgical apparatus.

21. A control device according to claim 20, wherein said medical and surgical apparatus comprises an artificial sphincter.

22. A control device according to claim 8, wherein said medical and surgical apparatus comprises an artificial sphincter.

* * * * *